(12) United States Patent
Hamada

(10) Patent No.: US 9,901,255 B2
(45) Date of Patent: Feb. 27, 2018

(54) MEDICAL IMAGE PROCESSING APPARATUS, METHOD OF OPERATING THE MEDICAL IMAGE PROCESSING APPARATUS, AND MEDICAL IMAGE PROCESSING PROGRAM

(71) Applicant: FUJIFILM Corporation, Tokyo (JP)

(72) Inventor: Akihiro Hamada, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 401 days.

(21) Appl. No.: 14/493,713

(22) Filed: Sep. 23, 2014

(65) Prior Publication Data

US 2015/0087954 A1 Mar. 26, 2015

(30) Foreign Application Priority Data

Sep. 25, 2013 (JP) ................................. 2013-197896

(51) Int. Cl.
| | | |
|---|---|---|
| *A61B 5/05* | (2006.01) | |
| *A61B 5/00* | (2006.01) | |
| *A61B 6/03* | (2006.01) | |
| *A61B 6/00* | (2006.01) | |
| *A61B 5/107* | (2006.01) | |

(52) U.S. Cl.
CPC .......... *A61B 5/0073* (2013.01); *A61B 5/1071* (2013.01); *A61B 5/7425* (2013.01); *A61B 5/7435* (2013.01); *A61B 6/032* (2013.01); *A61B 6/466* (2013.01); *A61B 6/5217* (2013.01); *A61B 6/5223* (2013.01)

(58) Field of Classification Search
CPC ..... A61B 5/0073; A61B 6/5223; A61B 6/466; A61B 5/7435; A61B 5/1071; A61B 6/5217; A61B 6/032; A61B 5/7425
USPC .......................... 600/407–480; 382/128–132
See application file for complete search history.

(56) References Cited

U.S. PATENT DOCUMENTS

| | | | | |
|---|---|---|---|---|
| 8,139,837 | B2 * | 3/2012 | Wang | G06T 7/0042 |
| | | | | 378/4 |
| 8,588,496 | B2 | 11/2013 | Wang et al. | |
| 8,737,705 | B2 | 5/2014 | Pearson, Jr. et al. | |
| 2007/0221233 | A1 * | 9/2007 | Kawano | A61B 1/00016 |
| | | | | 128/899 |

(Continued)

FOREIGN PATENT DOCUMENTS

| | | |
|---|---|---|
| JP | 4545807 B2 | 9/2010 |
| JP | 2011-030839 A | 2/2011 |

(Continued)

*Primary Examiner* — Sanjay Cattungal
(74) *Attorney, Agent, or Firm* — McGinn I.P. Law Group, PLLC.

(57) ABSTRACT

An organ region extracting section that extracts at least one organ region from a three dimensional image of a subject; a directional data obtaining section that obtains directional data of the subject based on one of the position of the organ region within the body of the subject and the shape of the organ region; a stage region extracting section that extracts a region of a stage on which the subject is placed from the three dimensional image; and a posture data obtaining section that obtains posture data of the subject on the stage, based on the region of the stage and the directional data of the subject; are provided.

20 Claims, 6 Drawing Sheets

(56) References Cited

U.S. PATENT DOCUMENTS

| | | | |
|---|---|---|---|
| 2008/0281189 A1* | 11/2008 | Komuro | A61B 5/06 600/424 |
| 2008/0306379 A1* | 12/2008 | Ikuma | A61B 5/06 600/424 |
| 2012/0059239 A1* | 3/2012 | Yamaguchi | G06T 7/20 600/407 |

FOREIGN PATENT DOCUMENTS

| | | |
|---|---|---|
| JP | 2011-160882 A | 8/2011 |
| JP | 2011-206297 A | 10/2011 |
| JP | 2013-052233 A | 3/2013 |

* cited by examiner

MEDICAL IMAGE PROCESSING APPARATUS, METHOD OF OPERATING THE MEDICAL IMAGE PROCESSING APPARATUS, AND MEDICAL IMAGE PROCESSING PROGRAM

CROSS REFERENCE TO RELATED APPLICATIONS

The present application claims priority under 35 USC § 119 to Japanese Patent Application No. 2013-197896 filed on Sep. 25, 2013. The above application is hereby expressly incorporated by reference in its entirety, into the present application.

BACKGROUND OF THE INVENTION

Technical Field

The present invention is related to a medical image processing apparatus, a method of operating the medical image processing apparatus, and a medical image processing program that obtain posture data of a subject based on a three dimensional image obtained by imaging the subject.

Background Art

Recently, lumen organs such as the large intestine, the small intestine, and the stomach of patients are extracted from three dimensional images imaged by modalities such as a CT (Computed Tomography) apparatus. The extracted three dimensional images of the lumen organs are employed to perform image diagnosis.

For example, it is possible to perform CT imaging in a state in which the large intestine is filled with air, and administer volume rendering on the three dimensional image obtained thereby from the interior of the large intestine, to generate images that simulate observation with an endoscope. Such images are referred to as virtual endoscopy images.

Here, in the case that residue is present within the large intestine when such virtual endoscopy images of the large intestine are generated and displayed, it will become difficult to find polyps which are present within the residue. This is because residue and polyps exhibit extremely similar CT values.

Therefore, both virtual endoscopy images based on a three dimensional image obtained by CT imaging in a supine posture and virtual endoscopy images based on a three dimensional image obtained by CT imaging in a prone posture are displayed on a display, in order to improve the detection accuracy with respect to polyps and the like. The positions of residue are different in a supine state and in a prone state due to gravity. Therefore, the entirety of the inner wall of the large intestine can be observed, by observing the two types of virtual endoscopy images.

Japanese Unexamined Patent Publication No. 2011-206297 and Japanese Unexamined Patent Publication No. 2011-030839 propose correlating positions within two virtual endoscopy images when displaying a virtual endoscopy image in a supine posture and a virtual endoscopy image in a prone posture as described above, to improve efficiency in image observation.

DISCLOSURE OF THE INVENTION

However, when displaying a virtual endoscopy image in a supine posture and a virtual endoscopy image in a prone posture as described above, it is necessary for a user to discriminate between the virtual endoscopy image in a supine posture and the virtual endoscopy image in a prone posture, by observing both of the virtual endoscopy images.

A method for discriminating between a virtual endoscopy image in a supine posture and a virtual endoscopy image in a prone posture, by inputting posture data regarding a subject when performing CT imaging, and appending the posture data to a three dimensional image, may be considered. However, there is a possibility that a user will input erroneous posture data, and the reliability of the posture data appended to three dimensional images will be low.

In addition, there are cases in which the aforementioned posture data cannot be appended to three dimensional images, depending on the imaging apparatus.

Japanese Unexamined Patent Publication No. 2013-052233 discloses automatic discrimination of the posture of a subject based on an image of the subject photographed by cameras. However, it is necessary for a plurality of cameras to be provided in this method, which will result in an increase in cost.

The present invention has been developed in view of the foregoing circumstances. It is an object of the present invention to provide a medical image processing apparatus, a method for operating the medical image processing apparatus, and a medical image processing program that automatically obtain posture data of a subject when a three dimensional image of the subject is imaged, without user input or an increase in cost.

A medical image processing apparatus of the present invention comprises:

an organ region extracting section that extracts at least one organ region from a three dimensional image of a subject;

a directional data obtaining section that obtains directional data of the subject based on one of the position of the organ region within the body of the subject and the shape of the organ region;

a stage region extracting section that extracts a region of a stage on which the subject is placed from the three dimensional image; and a posture data obtaining section that obtains posture data of the subject on the stage, based on the region of the stage and the directional data of the subject.

The medical image processing apparatus of the present invention may adopt a configuration, wherein:

the organ region extracting section extracts two organ regions; and the directional data obtaining section obtains the directional data of the subject based on the positional relationship between the two organ regions.

The organ region extracting section may extract bone regions as the organ regions.

The organ region extracting means may extract a breastbone region and a vertebral bone region as the bone regions, and the directional data obtaining section may obtain directional data regarding the anterior posterior direction of the subject based on the positional relationship between the breastbone region and the vertebral bone region.

Alternatively, the organ region extracting section may extract an organ region, which is present at a position shifted from the central axis of the subject in one of the anterior posterior direction and the horizontal direction; and the directional data obtaining section may obtain the directional data of the subject based on the positional relationship between the organ region and the surface of the body of the subject.

As a further alternative, the organ region extracting section may extract one of a breastbone region and a vertebral bone region as the organ region; and the directional data obtaining section may obtain directional data regarding the anterior posterior direction of the subject based on the positional relationship between one of the breastbone region and the vertebral bone region and the surface of the body of the subject.

As a still further alternative, the organ region extracting section may extract one of a heart region, a liver region, and a spleen region as the organ region; and the directional data may obtain directional data regarding the horizontal direction of the subject based on the positional relationship between the surface of the body of the subject and one of the heart region, the liver region, and the spleen region.

As a still yet further alternative, the organ region extracting section may extract a vertebral bone region as the organ region, and the directional data obtaining section may obtain directional data of the subject based on the shape of the vertebral bone region. As another alternative, the organ region extracting section may extract a right lung region and a left lung region as the organ regions; and the directional data obtaining section may obtain directional data regarding the horizontal direction of the subject based on the positional relationship between the right lung region and the left lung region.

In addition, the posture data obtaining section may obtain data indicating one of a supine position, a prone position, and a lateral position, as posture data of the subject.

Further, the posture data obtaining section may obtain directional data of the stage based on the region of the stage, and may obtain posture data of the subject based on the directional data of the stage.

A method for operating a medical image processing apparatus of the present invention is a method for operating a medical image processing apparatus equipped with an organ region extracting section, a directional data obtaining section, a stage region extracting section, and a posture data obtaining section, comprising:

the organ region extracting section extracting at least one organ region from a three dimensional image of a subject;

the directional data obtaining section obtaining directional data of the subject based on one of the position of the organ region within the subject and the shape of the organ region;

the stage region extracting section extracting a region of a stage on which the subject is placed from within the three dimensional image; and the posture data obtaining section obtaining posture data of the subject on the stage, based on the region of the stage and the directional data of the subject.

A medical image processing program of the present invention is stored in a non transitory computer readable medium, and causes a computer to function as:

an organ region extracting section that extracts at least one organ region from a three dimensional image of a subject;

a directional data obtaining section that obtains directional data of the subject based on one of the position of the organ region within the body of the subject and the shape of the organ region;

a stage region extracting section that extracts a region of a stage on which the subject is placed from the three dimensional image; and a posture data obtaining section that obtains posture data of the subject on the stage, based on the region of the stage and the directional data of the subject.

According to the medical image processing apparatus, the method of operating the medical image processing apparatus, and the medical image processing program of the present invention, at least one organ region is extracted from the three dimensional image of the subject, and directional data of the subject is obtained based on the position of the organ region within the subject or based on the shape of the organ region. Meanwhile, the region of a stage on which the subject is placed is extracted from the three dimensional image, and posture data of the subject on the stage is obtained based on the region of the stage and the directional data of the subject. Therefore, posture data of a subject when a three dimensional image is obtained can be automatically obtained without user input or an increase in cost.

BEST MODE FOR CARRYING OUT THE INVENTION

Figure 1:
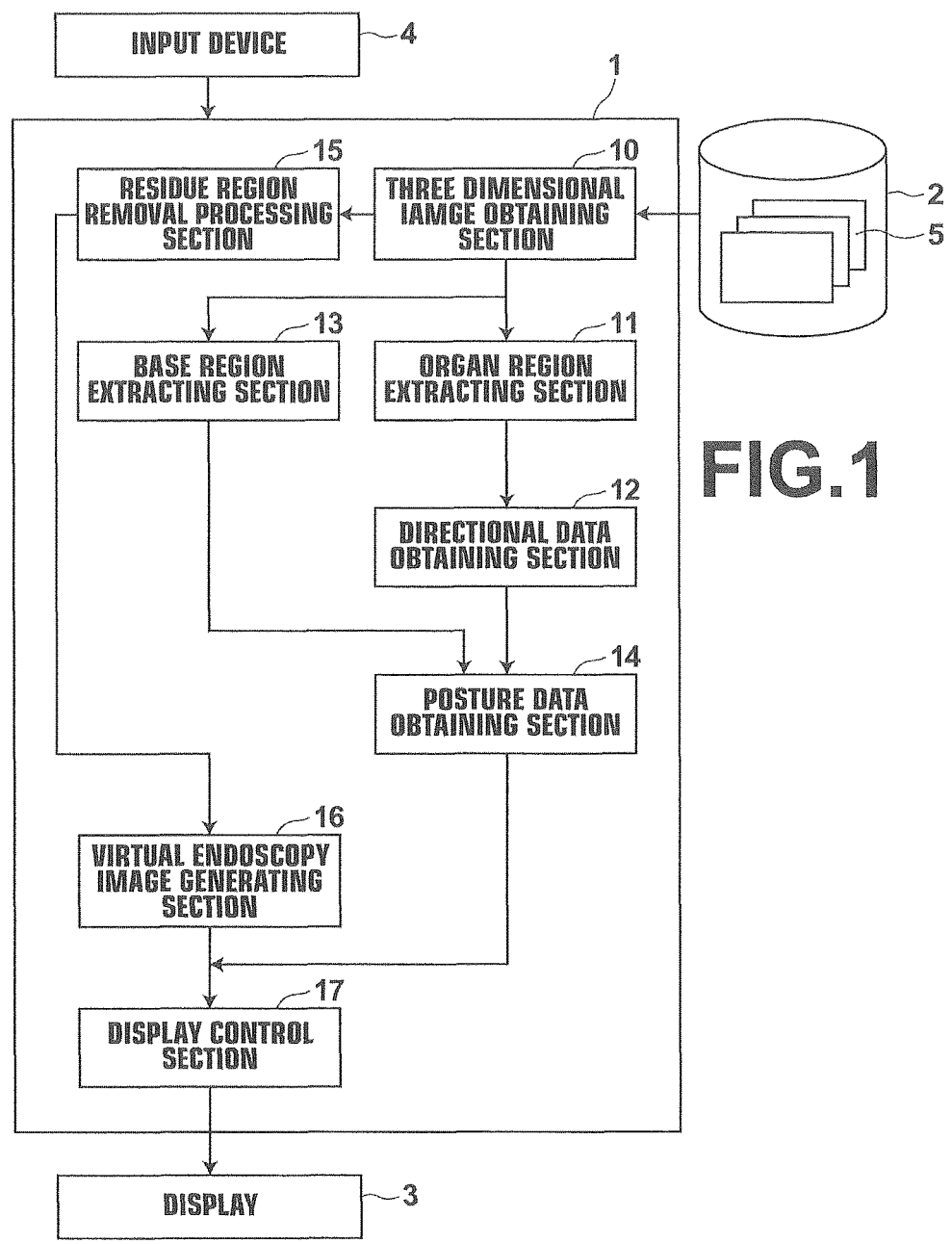
FIG. 1 is a block diagram that illustrates the schematic configuration of a medical image diagnosis assisting system that employs an embodiment of a medical image processing apparatus, the method of operating the medical image processing apparatus, and a medical image processing program of the present invention.

Hereinafter, a medical image diagnosis assisting system that employs an embodiment of a medical image processing apparatus, the method of operating the medical image processing apparatus, and a medical image processing program of the present invention will be described in detail with reference to the attached drawings. FIG. 1 is a block diagram that illustrates the schematic configuration of the medical image diagnosis assisting system of the present embodiment.

As illustrated in FIG. 1, the medical image diagnosis assisting system 1 of the present embodiment is equipped with a virtual endoscopy image display control apparatus 1, a three dimensional image storage server 2, a display 3, and an input device 4.

The virtual endoscopy image display control apparatus 1 is a computer, in which a virtual endoscopy image display program that includes the embodiment of the medical image processing program of the present invention is installed.

The virtual endoscopy image display control apparatus 1 is equipped with one or a plurality of central processing units (CPU's), a semiconductor memory, and storage devices, such as one or a plurality of hard disks or SSD's (Solid State Drives) The aforementioned virtual endoscopy image display program storage device is installed in the storage devices. A three dimensional image obtaining section 10, an organ region extracting section 11, a directional data obtaining section 12, a stage region extracting section 13, a posture data obtaining section 14, a residue region removal processing section 15, a virtual endoscopy image generating section 16 and a display control section 17 as illustrated in FIG. 1 function by the central processing unit executing the virtual endoscopy image display program. Note that the virtual endoscopy image display program may be that which is stored in a recording medium such as a CD-ROM, or may be that which is provided by SaaS (Software as a Service) via the Internet.

The three dimensional image obtaining section 10 obtains three dimensional images 5 of subjects, which are imaged in advance, prior to surgery, examinations, or the like. Examples of the three dimensional images 5 include volume data, which are reconstructed from slice data output from CT apparatuses, MRI (Magnetic Resonance Imaging) apparatuses, and the like, and volume data output from MS (MultiSlice) CT apparatuses and cone beam CT apparatuses.

Figure 2:
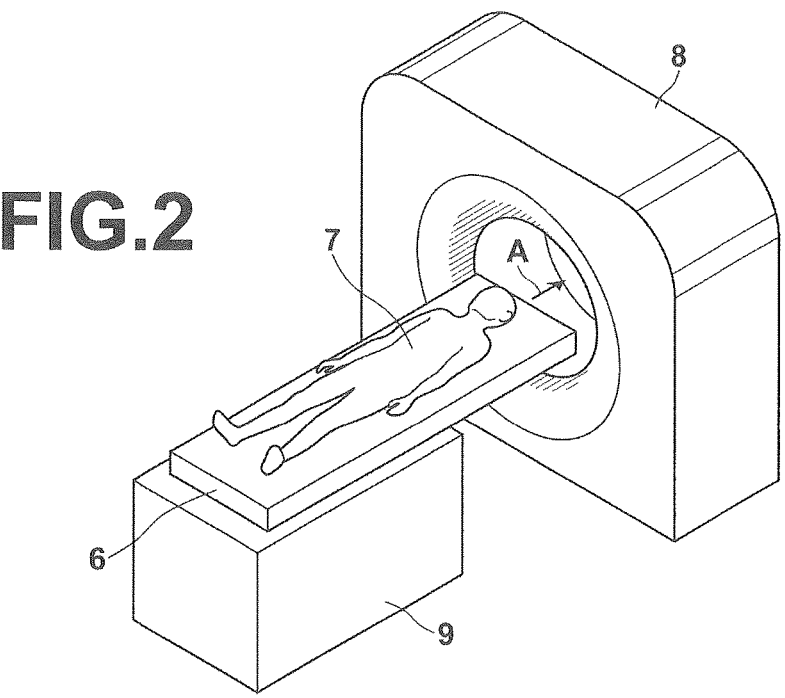
FIG. 2 is a diagram for explaining a three dimensional image which is imaged by a CT apparatus.

The three dimensional images 5 are obtained by causing a subject 7 to pass through a radiation irradiating apparatus 8 of a CT apparatus in a state in which the subject 7 is placed on a stage 6 as illustrated in FIG. 2, for example. Accordingly, the three dimensional images 5 include not only images of the subject 7, but also images of the stage 6. The stage 6 is constituted by a parallelepiped having a planar surface on which the subject 7 is placed, as illustrated in FIG. 2. The stage 6 is supported by a supporting base 9 so as to be movable in the direction of arrow A, and passes through the radiation irradiating apparatus 8 along with the subject 7. Accordingly, the three dimensional images 5 include images of the stage 6. Note that the stage 6 is formed by a material that appears as an image within the three dimensional images 5, that is, a material that absorbs radiation.

In addition, a person who is the subject 7 is placed in an upward facing state, that is, a supine position, in FIG. 2. However, imaging is not limited to such cases, and the subject 7 may be placed on the stage 6 in a prone state or a lateral recumbent state. That is, the three dimensional images 5 obtained by the three dimensional image obtaining section 10 are those imaged in one of a supine state, a prone state, and a lateral recumbent state.

The three dimensional images 5 are stored in the three dimensional image storage server 2 in advance, along with identifying data of subjects. The three dimensional image obtaining section 10 reads out three dimensional images 5 corresponding to identifying data of a subject which is input via the input device 4. Note that a configuration may be adopted, wherein the three dimensional image obtaining section 10 obtains a great number of pieces of slice data and generates volume data therefrom.

The three dimensional image storage server 2 may be a so called stand alone server device, or a so called cloud connected server device in which the three dimensional images are stored.

A three dimensional image 5 obtained by the three dimensional image obtaining section 10 is input to the organ region extracting section 11, and the organ region extracting section 11 extracts at least one organ region based on the three dimensional image 5 input thereto. The organ region is not limited to organ regions such as a heart region and a liver region, but also includes bone regions and a brain region.

Figure 3:
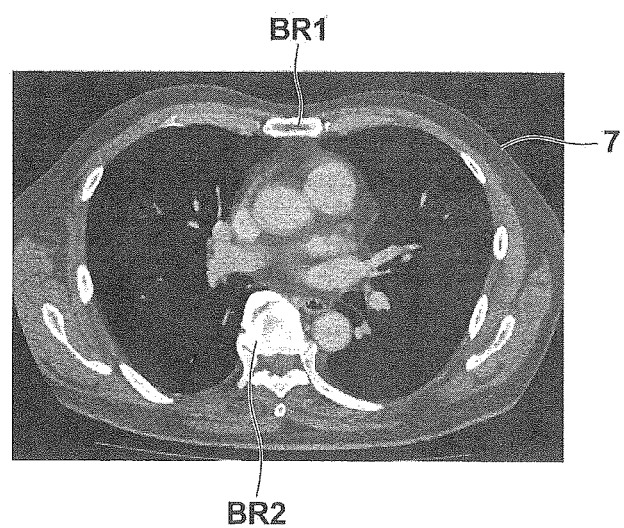
FIG. 3 is a diagram that illustrates an example of a breastbone region and a vertebral bone region.

Specifically, the organ region extracting section 11 of the present embodiment extracts a breastbone region BR1 and a vertebral bone region BR2 from a three dimensional image 5, as illustrated in FIG. 3. Note that FIG. 3 is an axial cross sectional view of the thorax of the subject 7. The method disclosed in Japanese Patent No. 4545807 may be employed as the method for extracting the breastbone region BR1 and the vertebral bone region BR2.

Specifically, the breastbone region appears as a rectangular region having an inner cavity (corpus spongiosum) having substantially the same thickness in each of a plurality of cross sectional images as illustrated in FIG. 3. Therefore, the breastbone region can be detected by performing pattern recognition. Note that the detection of the breastbone region may be performed for at least one tomographic image.

The vertebral bone region appears in tomographic images as a typical pattern in tomographic images, as illustrated in FIG. 3. Therefore, it is possible to stably detect the vertebral bone region from tomographic images. Specifically, a plurality of regions having predetermined sizes having each pixel within each tomographic image as centers thereof are set, and the vertebral bone region is detected by using a classifier generated by a machine learning technique to classify whether each region is a vertebral bone region. Note that the detection of the vertebral bone region may also be performed for at least one tomographic image.

Figure 4:
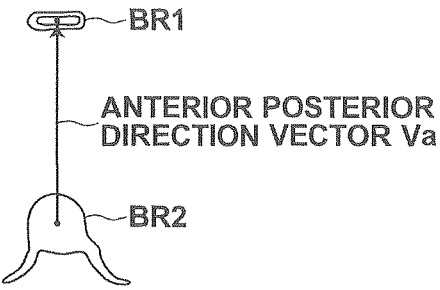
FIG. 4 is a diagram for explaining a method by which an anterior posterior direction vector is obtained based on a breastbone region and a vertebral bone region.

The method for extracting the breastbone region and the vertebral bone region is not limited to the method disclosed in Japanese Patent No. 4545807, and other known methods may be employed. The directional data obtaining section 12 obtains directional data of the subject 7, based on the position of the organ region extracted by the organ region extracting section 11 within the body of the subject. Specifically, the directional data obtaining section 12 of the present embodiment obtains data regarding the anterior posterior direction of the subject 7 based on the positional relationship between the breastbone region BR1 and the vertebral bone region BR2 which are extracted by the organ region extracting section 11. The breastbone region is positioned toward the front and at the approximate center in the horizontal direction of the subject 7. The vertebral bone region is positioned toward the rear and at the approximate center in the horizontal direction of the subject 7. Therefore, an anterior posterior direction vector Va can be obtained from a line that connects a feature point within the breastbone region BR1 and a feature point within the vertebral bone region BR2, as illustrated in FIG. 4. Note that the breastbone region BR1 and the vertebral bone region BR2 are those which are extracted from the same tomographic image. In addition, the center points or the barycenter points may be the feature points of the breastbone region BR1 and the vertebral bone region BR2. However, the present invention is not limited to such a configuration, and other structurally characteristic points may be the feature points.

The stage region extracting section 13 extracts a region of the stage 6, on which the subject 7 is placed, from the three dimensional image 5. The stage region extracting section 13 of the present embodiment extracts a subject region from the three dimensional image 5, and then extracts a non subject region by removing the extracted subject region from the three dimensional image 5 thereafter. Next, the stage region extracting section 13 extracts pixel values using a threshold value within a predetermined range from among each pixel value of the non subject region. Further, the stage region extracting section 13 administers a morphology process on the extracted pixel values, to extract the region of the stage 6. Note that in the present embodiment, extraction of the region of the stage 6 is performed for all tomographic images.

The method disclosed in Japanese Unexamined Patent Publication No. 2011-160882, for example, may be employed as the method for extracting the subject region from the three dimensional image. Alternatively, other known methods may be employed. In addition, the method for extracting the region of the stage 6 is not limited to the method described above, and other methods may be employed.

The posture data obtaining section 14 obtains posture data regarding the posture of the subject 7 on the stage 6, based on the region of the stage extracted by the stage region extracting section 13 and the anterior posterior direction vector Va of the subject 7 obtained by the directional data obtaining section 12.

Figure 5:
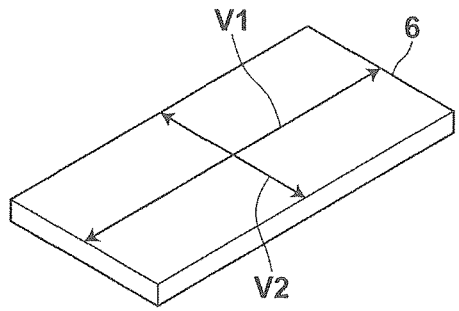
FIG. 5 is a diagram that illustrates a planar vector of a stage.

The posture data obtaining section 14 of the present embodiment calculates a planar vector of the stage 6 from the region of the stage 6. Specifically, principle component analysis is performed using the coordinate values of pixels (voxels) that constitute the region of the stage 6 as sample data, and the vectors of the top two components resulting from the analysis are obtained. A plane constituted by the vectors of these two components is designated as the plane of the stage 6. Note that FIG. 5 illustrates vectors V1 and V2 of the two components obtained by the aforementioned principal component analysis. As illustrated in FIG. 5, the vector V1, which is parallel to the long edge of the plane of the stage 6, and the vector V2, which is parallel to the short edge of the plane of the stage 6, are obtained.

Figure 6:
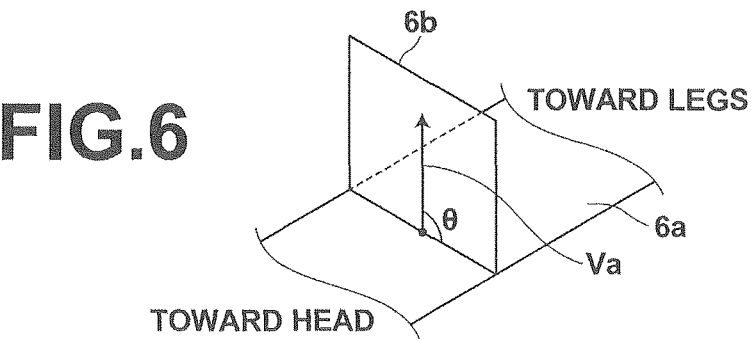
FIG. 6 is a diagram for explaining a method by which posture data is obtained based on directional data of a subject and directional data of the stage.

The posture data obtaining section 14 sets a projection plane 6b which intersects with the plane 6a of the stage 6 along a line which is parallel to the short edge thereof and is perpendicular to the plane 6a, as illustrated in FIG. 6. Then, the posture data obtaining section 14 projects the anterior posterior direction vector Va onto the projection plane 6a. Note that here, a drawing in which the starting point of the anterior posterior direction vector Va is moved perpendicular to the plane 6a is employed in order to facilitate understanding of the description.

Figure 7:
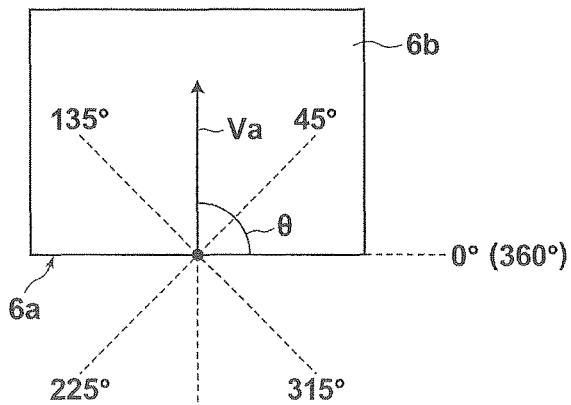
FIG. 7 is a diagram for explaining a method by which posture data is obtained based on directional data of a subject and directional data of the stage.

Next, the posture data obtaining section 14 obtains an angle θ formed by the anterior posterior direction vector Va projected onto the projection plane 6a and the plane 6a, and obtains posture data of the subject 7 based on the size of the angle θ. Specifically, the angle θ when the anterior posterior direction vector Va and the plane 6a are parallel, and the endpoint of the anterior posterior direction vector is oriented in the rightward direction is set as 0°. In the case that the angle θ is greater than 45° and less than 135°, a supine posture is obtained as the posture data. In the case that the angle θ is greater than or equal to 135° and less than or equal to 225°, a left lateral recumbent posture is obtained as the posture data. In the case that the angle θ is greater than 225° and less than 315°, a prone posture is obtained as the posture data. In the case that the angle θ is greater than or equal to 315° and less than or equal to 360° or greater than 0° and less than or equal to 45 degrees, a right lateral recumbent posture is obtained as the posture data. Note that the above description is for posture data for a case in which the side of projection plane 6b of FIG. 7 toward the viewer of the drawing sheet is the side toward the head of the subject 7, and the side of the projection plane 6b away from the viewer of the drawing sheet is the side toward the legs of the subject 7. In the case that the head side and the leg side with respect to the projection plane 6b are reversed, the discrimination results for the right lateral recumbent posture and the left lateral recumbent posture will be reversed.

The residue region removal processing section 15 detects tagged regions, in which residue present within the large intestine region are imaged, included in the three dimensional image 5, and administers a so called digital cleansing process to removed the tagged regions from the three dimensional image 5. The residue region removal processing section 15 detects the tagged regions by employing threshold value judgments, for example.

The virtual endoscopy image generating section 16 extracts a large intestine region from the three dimensional image 5 which has undergone the digital cleansing process administered by the residue region removal processing section 15, and generates a virtual endoscopy image that represents the inner walls of the large intestine employing the pixels within the extracted large intestine region.

Specifically, the virtual endoscopy image generating section 16 generates a centrally projected image, in which pixel data along light ray directions that extend radially from a line of sight vector based on a preset viewpoint and a line of sight direction are projected onto a predetermined projection plane, as the virtual endoscopy image. Note that a known volume rendering technique or the like may be employed as the specific method for central projection.

In addition, the viewpoint of the virtual endoscopy image may be set by a user employing the input device 4 to specify a desired point within a three dimensional image of the large intestine which is being displayed on the display 3. Alternatively, a predetermined point along the center line of the large intestine, which is extracted based on pixel data of the large intestine, may be specified automatically or manually. In addition, the line of sight direction may be manually set to a desired direction by a user. Alternatively, the progression direction of the center line of the large intestine may be set as the line of sight direction. Note that methods for extracting large intestine regions and methods for generating virtual endoscopy images are known, and therefore detailed descriptions thereof will be omitted.

The display control section 17 causes the virtual endoscopy image generated by the virtual endoscopy image generating section 16 and the posture data obtained by the posture data obtaining section 14 to be displayed on the display 3 together. In addition, the display control section 17 also causes three dimensional images of the large intestine region and tomographic images of the subject 7 to be displayed on the display 3, in addition to the virtual endoscopy image.

In addition, the display control section 17 may cause two or more virtual endoscopy images, which are generated from three dimensional images 5 obtained with a subject 7 in different postures, to be simultaneously displayed on the display, together with posture data of the subject 7 corresponding to each of the virtual endoscopy images. For example, a virtual endoscopy image of the subject in a supine posture may be displayed on the display together with posture data indicating the supine posture, simultaneously with a virtual endoscopy image of the subject in a prone posture may be displayed on the display together with posture data indicating the prone posture.

The input device 4 is equipped with a mouse, a keyboard, and the like, and receives operative input from a user. Specifically, the input device 4 receives input of the viewpoint and the line of sight direction when generating virtual endoscopy images as described above.

Figure 8:
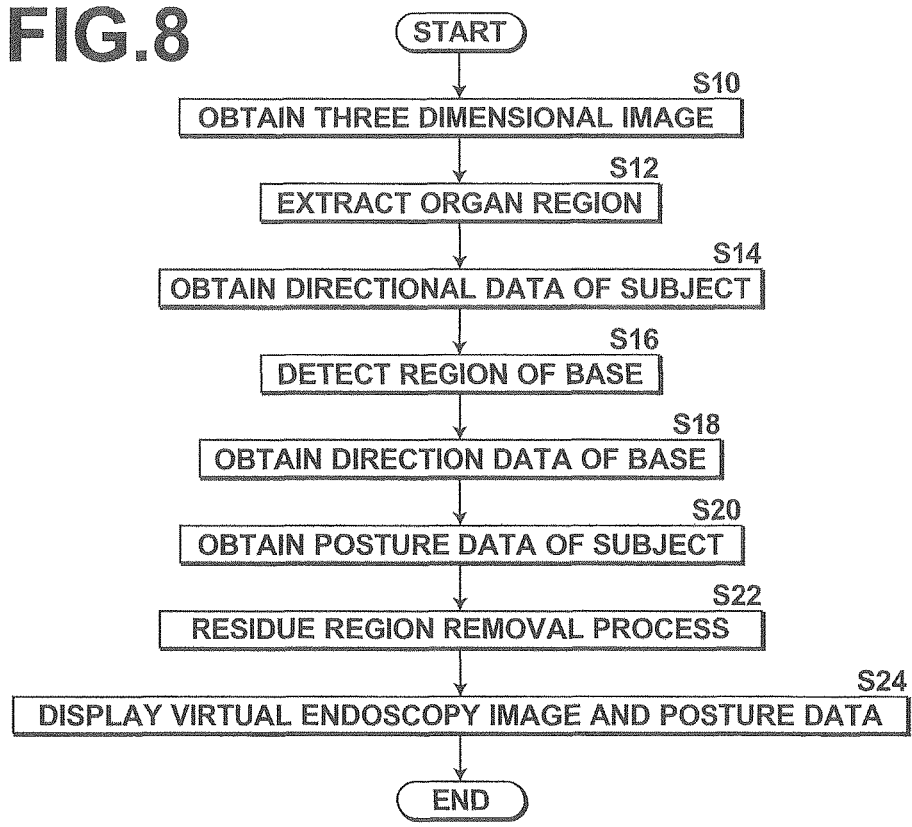
FIG. 8 is a flow chart for explaining the operations of the medical image diagnosis assisting system illustrated in FIG. 1.

Next, the operation of the medical image diagnosis assisting system of the present embodiment will be described with reference to the flow chart of FIG. 8.

First, identifying data regarding a subject is input by a user employing the input device 4, and the three dimensional image obtaining section 10 of the virtual endoscopy image display control apparatus 1 reads out and obtains a three dimensional image 5 corresponding to the input identifying data (S10).

The three dimensional image 5 obtained by the three dimensional image obtaining section 10 is input to the organ region extracting section 11, and the organ region extracting section 11 extracts the aforementioned breastbone region BR1 and the vertebral region BR2, based on the input three dimensional image 5 (S12).

Next, the breastbone region BR1 and the vertebral bone region BR2 are input to the directional data obtaining section 12, and the directional data obtaining section 12 obtains the anterior posterior direction vector Va that connects the center point of the breastbone region BR1 and the center point of the vertebral bone region BR2 (S14).

Meanwhile, the three dimensional image 5 obtained by the three dimensional image obtaining section 10 is also input to the stage region extracting section 13, and the stage region extracting section 13 extracts the region of the stage 6 based on the input three dimensional image 5 in the manner described above (S16).

Next, the anterior posterior direction vector Va of the subject 7 obtained by the directional data obtaining section 12 and the region of the stage 6 extracted by the stage region extracting section 13 are input to the posture data obtaining section 14, and the posture data obtaining section 14 obtains the posture data of the subject 7 based on the input data in the manner described above (S18, S20). The posture data obtained by the posture data obtaining section 14 is output to the display control section 17.

In addition, the three dimensional image 5 obtained by the three dimensional image obtaining section 10 is input to the residue region removal processing section 15, the residue region removal processing section 15 administers a digital cleansing process on the input three dimensional image 5, then outputs the processed three dimensional image 5 to the virtual endoscopy image generating section 16 (S22).

The three dimensional image 5 on which the digital cleansing process has been administered is input to the virtual endoscopy image generating section 16. The virtual endoscopy image generating section 16 generates a virtual endoscopy image, based on the preset viewpoint, the preset line of sight direction, and the three dimensional image 5 which has undergone the digital cleansing process. The virtual endoscopy image and the posture data obtained by the posture data obtaining section 14 are input to the display control section 17, and are displayed on the display 3 (S24).

According to the medical image diagnosis assisting system of the present embodiment, the organ regions are extracted from the three dimensional image 5 of the subject 7, and directional data of the subject is obtained based on the positions of the organ regions within the subject. Meanwhile, the region of a stage on which the subject is placed is extracted from the three dimensional image, and posture data of the subject on the stage is obtained based on the region of the stage and the directional data of the subject. Therefore, posture data of a subject when a three dimensional image is obtained can be automatically obtained without user input or an increase in cost.

In addition, by simultaneously displaying the posture data obtained in the manner described above and the virtual endoscopy image generated based on the three dimensional image, the posture of the subject within the three dimensional image on which the virtual endoscopy image is based can be instantly understood, leading to an improvement in efficiency of diagnosis.

Figure 9:
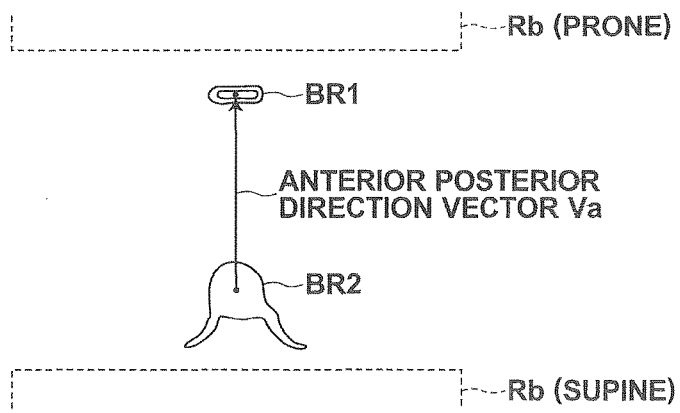
FIG. 9 is a diagram for explaining an example of another method by which posture data is obtained based on directional data of a subject and directional data of the stage.

Note that in the above embodiment, a case was described in which the angle θ formed by the anterior posterior direction vector Va and the plane 6a of the stage 6 is obtained, and the posture data of the subject 7 is obtained based on the size of the angle θ. However, the present invention is not limited to such a configuration. In the case that only discrimination of whether a subject is supine or prone is necessary, for example, posture data indicating a supine posture or a prone posture may be obtained based on whether the region Rb of the stage 6 is toward the side of the breastbone region BR1 or toward the side of the vertebral bone region BR2 along the anterior posterior direction vector Va based on the breastbone region BR1 and the vertebral bone region BR2, as illustrated in FIG. 9. That is, the posture data obtaining section 14 may obtain posture data indicating a prone posture in the case that the region Rb of the stage 6 is toward the side of the breastbone region BR1, and obtain posture data indicating a supine posture in the case that the region Rb of the stage 6 is toward the side of the vertebral bone region BR2.

Figure 10:
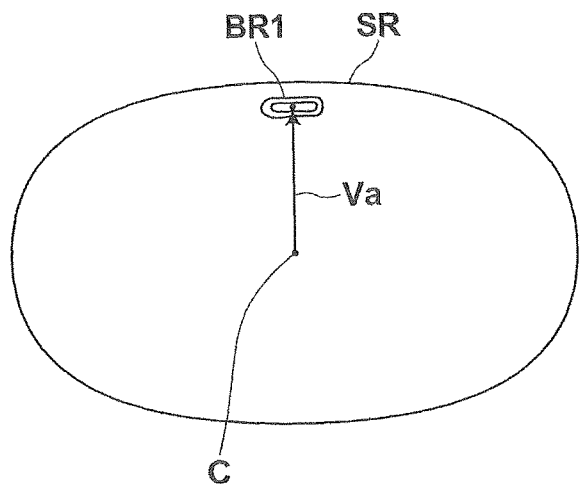
FIG. 10 is a diagram for explaining an example of another method by which an anterior posterior direction vector is obtained.

In addition, in the above embodiment, the anterior posterior direction vector Va is obtained based on the breastbone region BR1 and the vertebral bone region BR2. However, other methods may be employed to obtain the anterior posterior direction vector Va. Specifically, a body surface region SR may be extracted from the three dimensional image 5 of the subject 7 as illustrated in FIG. 10. Then, the anterior posterior direction vector Va may be obtained based on a line that connects the central axis (center point) C of the body surface region SR and the center point of the breastbone region BR1. The method disclosed in Japanese Unexamined Patent Publication No. 2011-160882, for example, may be employed to extract the body surface region SR. With respect to the central axis of the body surface region SR, the body surface region SR may be approximated by an elliptical shape, and the center of the elliptical shape may be obtained as the central axis. Alternatively, the body surface region SR may be approximated by a different shape, and the barycenter of the different shape may be obtained as the central axis. Note that FIG. 10 is an axial tomographic image of the thorax of the subject 7.

Figure 11:
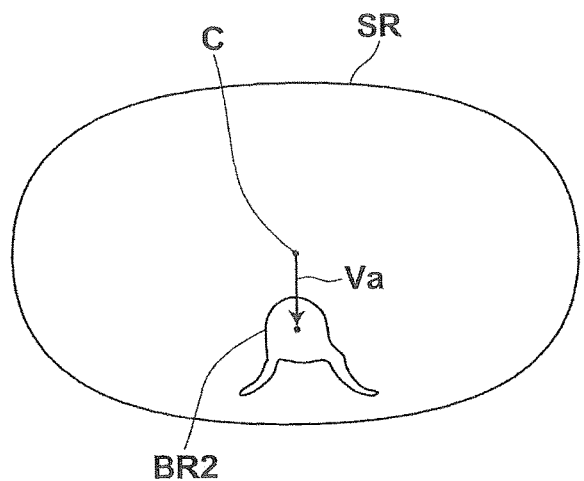
FIG. 11 is a diagram for explaining an example of another method by which an anterior posterior direction vector is obtained.

Alternatively, the anterior posterior direction vector Va may be obtained based on a line that connects the central axis (center point) C of the body surface region SR and the vertebral bone region BR2, as illustrated in FIG. 11.

Figure 12:
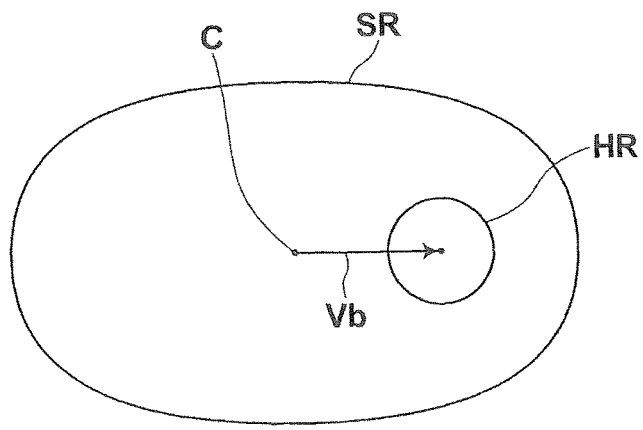
FIG. 12 is a diagram for explaining a method by which a horizontal direction vector of a subject is obtained, based on the surface of the body of a subject and a heart region.

In addition, in the embodiment above, directional data of the subject 7 was obtained based on the positions of bone regions, such as the breastbone region and the vertebral bone region. However, the organ regions to be extracted are not limited to bone regions. Organ regions which are present at positions shifted from the central axis of the subject 7 in the horizontal direction, such as a heart region and a liver region, may be extracted. Then, directional data of the subject 7 may be obtained based on the positional relationship between the extracted organ regions and the central axis of the body surface region SR of the subject 7. Specifically, a heart region HR may be extracted from a three dimensional image 5 of the subject 7, as illustrated in FIG. 12. Then, a horizontal direction vector Vb of the subject 7 may be obtained based on a line that connects the central axis (center point) C of the body surface region SR and the center point of the heart region HR. Note that FIG. 12 is an axial tomographic image of the thorax of the subject 7. Alternatively, the apex of the heart, which represents the tip of the heart, may be extracted, and the horizontal direction vector Vb may be obtained based on a line that connects the central axis of the body surface region SR and the apex of the heart, instead of the center point of the heart region HR.

It is possible to obtain posture data of the subject based on an angle θ formed between the horizontal direction vector Vb and the plane 6a of the stage 6 in the case that the horizontal direction vector Vb of the subject 7 is obtained as well. Note that in the case that the horizontal direction vector Vb is obtained, a supine posture is obtained as the posture data in the case that the angle θ is greater than or equal to 315° and less than or equal to 360° or greater than 0° and less than or equal to 45 degrees, for example. In the case that the angle θ is greater than 45° and less than 135°, a right lateral recumbent posture is obtained as the posture data. In the case that the angle θ is greater than or equal to 135° and less than or equal to 225°, a prone posture is obtained as the posture data. In the case that the angle θ is greater than 225° and less than 315°, a left lateral recumbent posture is obtained as the posture data.

In addition, the organ region to be extracted is not limited to the aforementioned heart region. For example, a liver region or a spleen region may be extracted, and the horizontal direction vector of the subject 7 may be obtained based on a line that connects the central axis (center point) C of the body surface region SR and the barycenter of the liver region or the spleen region. As a further alternative, a right lung region and a left lung region may be extracted as the organ regions, and the horizontal direction vector of the subject 7 may be obtained based on the positional relationship between the right lung region and the left lung region. Specifically, feature points such as the barycenter may be obtained within each of the right lung region and the left lung region, and the horizontal direction vector may be obtained based on a line that connects the feature points. The feature points are not limited to the barycenter, and other feature points unique to the shapes of the lungs may be employed. Note that the right lung is constituted by three regions, which are an upper lobe, a middle lobe, and a lower lobe, whereas the left lung is constituted by two regions, which are an upper lobe and a lower lobe. Therefore, the right lung region and the left lung region can be distinguished based on this difference in structure, and thereby the leftward direction and the rightward direction can be discriminated. The right lung region and the left lung region may be extracted by employing known methods.

Figure 13:
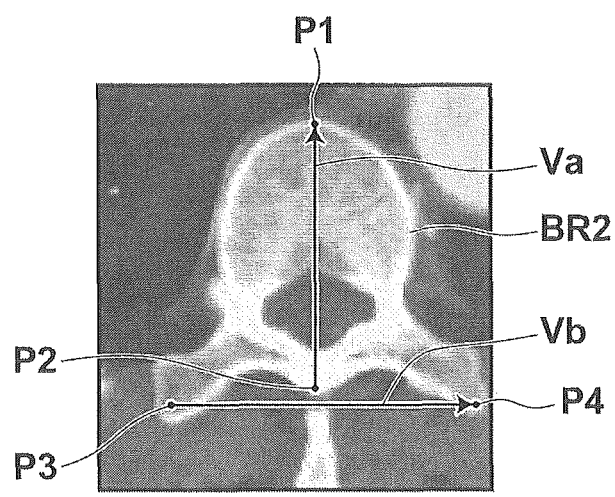
FIG. 13 is a diagram for explaining a method by which an anterior posterior direction vector or a horizontal direction vector of a subject is obtained based on the shape of a vertebral bone region.

In addition, the directional data of the subject 7 are obtained based on the positional relationship between two organ regions or the positional relationship between the body surface region and one organ region in the above description. However, the present invention is not limited to such a configuration, and an anterior posterior direction vector or a horizontal direction vector may be obtained based on the shape of a single organ region. Specifically, only the vertebral bone region BR2 may be extracted from the three dimensional image 5 of the subject 7 as illustrated in FIG. 13. The anterior posterior direction vector Va may be obtained based on a line that connects a feature point P1 and a feature point P2 regarding the anterior posterior direction. Alternatively, the horizontal direction vector Vb may be obtained based on a line that connects a feature point P3 and a feature point P4 regarding the horizontal direction. Note that the feature point P1 through the feature point P4 may be specified by performing pattern matching between a vertebral bone region pattern, in which points corresponding to the feature point P1 through the feature point P2 are set, and the vertebral bone region BR2 which is actually extracted.

Further, in the above embodiment, the posture data of the subject 7 obtained by the posture data obtaining section 14 is displayed together with the virtual endoscopy image. However, use of the posture data is not limited to such display. For example, when extracting an organ region, such as a large intestine region and a heart region, from a three dimensional image of the subject 7, there are cases in which the manners of deformation of the organ region differ depending on the posture of the subject. Therefore, the extraction process may be performed employing the posture data of the subject 7, when extracting an organ region, such as a large intestine region and a heart region, from a three dimensional image of the subject 7.

What is claimed is:

1. A medical image processing apparatus, comprising:
   an organ region extracting section that extracts at least one organ region from a three dimensional image of a subject;
   a directional data obtaining section that obtains directional data including a direction vector of the subject based on one of the position of the organ region within the body of the subject and the shape of the organ region;
   a stage region extracting section that extracts a region of a stage on which the subject is placed from the three dimensional image; and
   a posture data obtaining section that obtains posture data of the subject on the stage, based on the region of the stage and the directional data of the subject,
   wherein the posture data is obtained solely based on data extracted out of the three dimensional image of the subject.

2. A medical image processing apparatus as defined in claim 1, wherein:
   the organ region extracting section extracts two organ regions; and
   the directional data obtaining section obtains the directional data of the subject based on the positional relationship between the two organ regions.

3. A medical image processing apparatus as defined in claim 2, wherein:
   the organ region extracting section extracts bone regions as the organ regions.

4. A medical image processing apparatus as defined in claim 3, wherein:
   the organ region extracting section extracts a breastbone region and a vertebral bone region; and
   the directional data obtaining section obtains directional data regarding the anterior posterior direction of the subject based on the positional relationship between the breastbone region and the vertebral bone region.

5. A medical image processing apparatus as defined in claim 2, wherein:

the organ region extracting section extracts a right lung region and a left lung region as the organ regions; and the directional data obtaining section obtains directional data regarding the horizontal direction of the subject based on the positional relationship between the right lung region and the left lung region.

6. A medical image processing apparatus as defined in claim 1, wherein:

the organ region extracting section extracts an organ region, which is present at a position shifted from the central axis of the subject in one of the anterior posterior direction and the horizontal direction; and the directional data obtaining section obtains the directional data of the subject based on the positional relationship between the organ region and the surface of the body of the subject.

7. A medical image processing apparatus as defined in claim 6, wherein:

the organ region extracting section extracts a bone region as the at least one organ region.

8. A medical image processing apparatus as defined in claim 7, wherein:

the organ region extracting section extracts one of a breastbone region and a vertebral bone region as the organ region; and the directional data obtaining section obtains directional data regarding the anterior posterior direction of the subject based on the positional relationship between one of the breastbone region and the vertebral bone region and the surface of the body of the subject.

9. A medical image processing apparatus as defined in claim 6, wherein:

the organ region extracting section extracts one of a heart region, a liver region, and a spleen region as the organ region; and the directional data obtains directional data regarding the horizontal direction of the subject based on the positional relationship between the surface of the body of the subject and one of the heart region, the liver region, and the spleen region.

10. A medical image processing apparatus as defined in claim 1, wherein:

the organ region extracting section extracts a vertebral bone region as the organ region; and the directional data obtaining section obtains directional data of the subject based on the shape of the vertebral bone region.

11. A medical image processing apparatus as defined in claim 1, wherein:

the posture data obtaining section obtains data indicating one of a supine position, a prone position, and a lateral position, as posture data of the subject.

12. A medical image processing apparatus as defined in claim 1, wherein:

the posture data obtaining section obtains directional data of the stage based on the region of the stage, and obtains posture data of the subject based on the directional data of the stage.

13. The medical image processing apparatus as defined in claim 1, wherein the stage region extracting section extracts the subject region from the three dimensional image, and then extracts a non-subject region by removing the extracted subject region from the three dimensional image.

14. The medical image processing apparatus as defined in claim 13, wherein the stage region extracting section extracts pixel values using a threshold value within a predetermined range from among each pixel value of the non-subject region, and wherein the stage region extracting section morphs the extracted pixel values to extract the region of the stage.

15. The medical image processing apparatus as defined in claim 1, wherein the posture data obtaining section calculates a planar vector as the direction vector of the stage from the region of the stage.

16. The medical image processing apparatus as defined in claim 15, wherein the posture data obtaining section performs a component analysis using coordinate values of pixels of the region of the stage as sample data, wherein the posture data obtaining section obtains vectors of two components resulting from the component analysis, wherein a plane constituted by the vectors of the two components is designated as the plane of the stage.

17. The medical image processing apparatus as defined in claim 16, wherein the posture data obtaining section sets a projection plane which intersects with the plane of the stage along a line which is parallel to a short edge of the stage and is perpendicular to the plane, wherein the posture data obtaining section projects the direction vector onto the projection plane, and wherein the posture data obtaining section obtains an angle formed by the direction vector projected onto the projection plane and the plane and obtains the posture data of the subject based on a size of the angle.

18. The medical image processing apparatus as defined in claim 1, wherein the posture data obtaining section sets a projection plane which intersects with the plane of the stage along a line which is parallel to a short edge of the stage and is perpendicular to the plane, wherein the posture data obtaining section projects the direction vector onto the projection plane, and wherein the posture data obtaining section obtains an angle formed by the direction vector projected onto the projection plane and the plane and obtains the posture data of the subject based on a size of the angle.

19. A method for operating a medical image processing apparatus equipped with an organ region extracting section, a directional data obtaining section, a stage region extracting section, and a posture data obtaining section, comprising:

the organ region extracting section extracting at least one organ region from a three dimensional image of a subject;

the directional data obtaining section obtaining directional data including a direction vector of the subject based on one of the position of the organ region within the subject and the shape of the organ region;

the stage region extracting section extracting a region of a stage on which the subject is placed from within the three dimensional image; and the posture data obtaining section obtaining posture data of the subject on the stage, based on the region of the stage and the directional data of the subject, wherein the posture data is obtained solely based on data extracted out of the three dimensional image of the subject.

20. A non transitory computer readable medium having a medical image processing program stored therein, the medical image processing program causing a computer to function as:

an organ region extracting section that extracts at least one organ region from a three dimensional image of a subject;

a directional data obtaining section that obtains directional data including a direction vector of the subject based on one of the position of the organ region within the body of the subject and the shape of the organ region;
a stage region extracting section that extracts a region of a stage on which the subject is placed from the three dimensional image; and
a posture data obtaining section that obtains posture data of the subject on the stage, based on the region of the stage and the directional data of the subject,
an organ region extracting section that extracts at least one organ region from a three dimensional image of a subject,
wherein the posture data is obtained solely based on data extracted out of the three dimensional image of the subject.

* * * * *